United States Patent [19]

Muller et al.

[11] Patent Number: 4,549,019

[45] Date of Patent: Oct. 22, 1985

[54] PYRIMIDINECARBAMATE DERIVATIVES AS INTERMEDIATES

[75] Inventors: Jean-Claude Muller, Rixheim, France; Henri Ramuz, Birsfelden, Switzerland

[73] Assignee: Hoffmann-La Roche Inc., Nutley, N.J.

[21] Appl. No.: 394,392

[22] Filed: Jul. 1, 1982

[30] Foreign Application Priority Data

Jul. 15, 1981 [CH] Switzerland .................. 4640/81
Mar. 12, 1982 [CH] Switzerland .................. 1559/82

[51] Int. Cl.$^4$ .................................. C07D 239/34
[52] U.S. Cl. .................................. 544/321; 544/255; 544/298; 544/320; 544/323; 548/262; 548/333; 548/341
[58] Field of Search .............. 544/320, 321, 323; 424/250

[56] References Cited

U.S. PATENT DOCUMENTS

| | | | |
|---|---|---|---|
| 3,382,248 | 5/1968 | Anthony et al. | 544/321 |
| 3,435,035 | 3/1969 | Habicht et al. | 544/321 |
| 4,150,132 | 4/1979 | Müller et al. | 544/323 |
| 4,176,119 | 11/1979 | Müller et al. | 544/323 |
| 4,220,772 | 9/1980 | Müller et al. | 544/323 |

FOREIGN PATENT DOCUMENTS 2943161 5/1980 Fed. Rep. of Germany .
2032434 5/1980 United Kingdom .

Primary Examiner—Richard L. Raymond
Assistant Examiner—James H. Turnipseed
Attorney, Agent, or Firm—Jon S. Saxe; Bernard S. Leon; William G. Isgro

[57] ABSTRACT

2,4-Disubstituted 6-[3,6-dihydro-1(2H)-pyridyl]pyrimidine-3-oxides of the formula

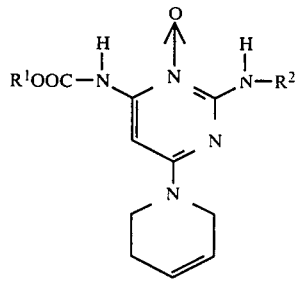

wherein $R^1$ is lower alkyl or lower alkoxy-lower alkyl, $R^2$ is hydrogen or —COOR$^3$ wherein $R^3$ is lower alkyl or lower alkoxy-lower alkyl, which are important for the preparation of therapeutically valuable 1,2,5,6-tetrahydropyridyl-substituted 2-oxo-2H-[1,2,4]oxadiazolopyrimidinecarbamates, are described. The foregoing oxides of formula I can be prepared by reacting the corresponding arylsulfonyloxy- or alkylsulfonyl-substituted derivatives with 1,2,5,6-tetrahydropyridine.

5 Claims, No Drawings

PYRIMIDINECARBAMATE DERIVATIVES AS INTERMEDIATES

BRIEF SUMMARY OF THE INVENTION

The invention relates to compounds of the formula

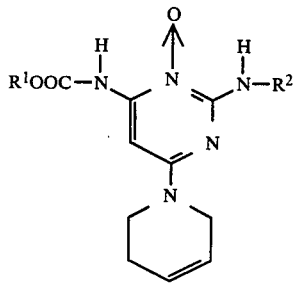

wherein $R^1$ is lower alkyl or lower alkoxy-lower alkyl, $R^2$ is hydrogen or $-COOR^3$ wherein $R^3$ is lower alkyl or lower alkoxy-lower alkyl,
which are useful as intermediates for the preparation of therapeutically valuable 1,2,5,6-tetrahydropyridyl-substituted 2-oxo-2H-[1,2,4]oxadiazolopyrimidinecarbamates. The compounds of formula I are obtained by reacting the corresponding arylsulfonyloxy- or alkylsulfonyloxy-substituted derivatives with 1,2,5,6-tetrahydropyridine.

DETAILED DESCRIPTION OF THE INVENTION

The invention relates to a process for the preparation of 2,4-disubstituted 6-[3,6-dihydro-1(2H)-pyridyl]-pyrimidine-3-oxides of the formula

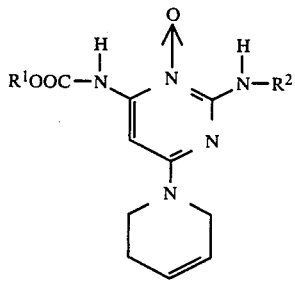

wherein $R^1$ is lower alkyl or lower alkoxy-lower alkyl, $R^2$ is hydrogen or $-COOR^3$ wherein $R^3$ is lower alkyl or lower alkoxy-lower alkyl, and $R^1$ and $R^3$ can be the same or different.

The term "lower alkyl" used in this description, alone or in combination, denotes straight-chain and branched-chain saturated hydrocarbon groups containing 1–8 carbon atoms, for example, methyl, ethyl, n-propyl, isopropyl, n-butyl, isobutyl, tert.butyl and the like. The term "lower alkoxy" denotes lower ether groups in which "lower alkyl" has the significance given earlier. Examples of "arylsulfonyloxy" are p-toluenesulfonyloxy, benzene-sulfonyloxy and p-bromobenzenesulfonyloxy and the like; examples of "alkylsulfonyloxy" are mesyloxy and the like.

The preparation of compounds of formula I in which $R^1$ is lower alkyl and $R^2$ is hydrogen is preferred. The preparation of those compounds of formula I in which $R^1$ is alkyl containing 1–4 carbon atoms and $R^2$ is hydrogen is especially preferred. The preparation of the compound of formula I in which $R^1$ is methyl and $R^2$ is hydrogen, that is, of methyl 2-amino-6-[3,6-dihydro-1(2H)-pyridyl]-4-pyrimidinecarbamate-3-oxide, is particularly preferred.

The compounds of formula I are important intermediates for the preparation of therapeutically valuable compounds, for example, for the preparation of oxadiazolopyrimidine derivatives of the formula

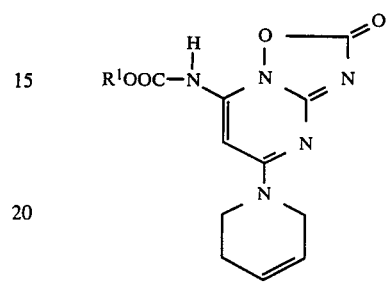

wherein $R^1$ is as previously described.

The compounds of formula II are known and can be used for the treatment of vascular-conditioned hypertensions or as vasodilators in peripheral blood supply disorders. The conversion of the compounds of formula I in which $R^2$ is hydrogen into the oxadiazolopyrimidine derivatives of formula II can be carried out in a known manner by reaction with phosgene. The conversion of the compounds of formula I in which $R^2$ is $-COOR^3$ into the oxadiazolopyrimidine derivatives of formula II can be carried out in a known manner by cyclization. Compounds of formula I in which $R^2$ is hydrogen can also be converted into the oxadiazolopyrimidine derivatives of formula II by reaction with a chloroformic acid ester of the formula

Cl—COOR³       III wherein $R^3$ is as previously described,
and cyclization of the resulting corresponding compound of formula I in which $R^2$ is $-COOR^3$, that is, of the di-carbamate of the formula

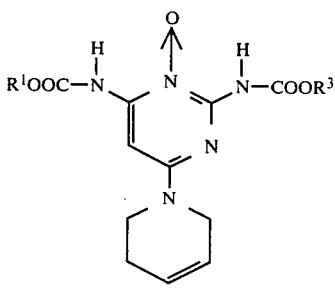

wherein $R^1$ and $R^3$ are as previously described.

The compounds of formula I can be prepared in accordance with the invention by reacting a compound of the formula

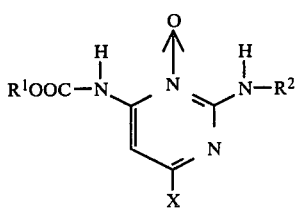

wherein X is arylsulfonyloxy or alkylsulfonyloxy and $R^1$ and $R^2$ are as previously described, with 1,2,5,6-tetrahydropyridine.

The reaction of a compound of formula IV with 1,2,5,6-tetrahydropyridine is carried out in a known manner in the presence of an inert solvent or solvent mixture. As solvents there come into consideration chlorinated hydrocarbons, such as, methylene chloride or chloroform, aromatic hydrocarbons, such as, toluene or xylene, and the like or mixtures thereof. The reaction is preferably carried out in an inert gas atmosphere, preferably under argon or nitrogen, at a temperature in the range of from about 0° to about 50° C., preferably at room temperature. Excess 1,2,5,6-tetrahydropyridine can also be used in place of an inert solvent.

The compounds of formula IV also form part of the invention. The compounds of formula IV and their chloro analogs that is, compounds which correspond to formula IV but in which X is chlorine, can be prepared by selectively oxidizing a compound of the formula

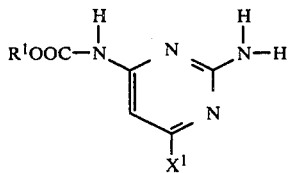

wherein $X^1$ is chlorine, arylsulfonyloxy or alkylsulfonyloxy and $R^1$ is as previously described, and, if desired, reacting the compound obtained with a chloroformic acid ester of formula III hereinbefore.

The selective oxidation is carried out in a known manner by reaction with a peracid in an inert organic solvent at a temperature in the range of from about 0° to about 80° C., preferably in the range of from about room temperature to about 50° C. Peracetic acid, perbenzoic acid, m-chloroperbenzoic acid, trifluoroperacetic acid and the like are suitable peracids for the present purpose. As inert organic solvents there come into consideration chlorinated hydrocarbons, such as, methylene chloride or chloroform, hydrocarbons, such as, hexane or cyclohexane, aromatic hydrocarbons, such as, benzene or toluene, and the like.

The optional reaction of the resulting compound of the formula

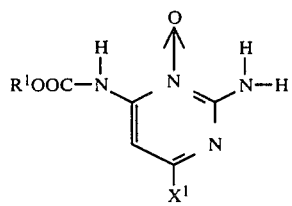

wherein $R^1$ and $X^1$ are as previously described, with the chloroformic acid ester of formula III is similarly carried out in a known manner, conveniently in an organic solvent or solvent mixture which is inert under the reaction conditions, for example, chlorinated hydrocarbons, such as, methylene chloride, chloroform or the like, ethers, such as, diethyl ether, tetrahydrofuran, dioxane or the like, dimethylformamide or the like, or mixtures thereof and/or with water and in the presence of a base, for example, tertiary amines, such as, triethylamine, ethyldiisopropylamine, trimethylamine, N-methylmorpholine, pyridine or the like, alkali metal carbonates, such as, sodium bicarbonate or the like, alkali metal hydroxides such as sodium hydroxide, potassium hydroxide or the like, if a liquid base is used, then this can also serve as the solvent. The reaction is conveniently carried out at a temperature in the range of from about 0° to about room temperature, preferably in the range of from about 0° to about 10° C.

The compounds of formula V also form part of the invention. A process for the preparation of the compounds of formula V is illustrated in Schemes I and II hereinafter in which $R^1$ and X are as previously described. With respect to the precise reaction conditions reference is made to the Examples which follow.

Scheme 1

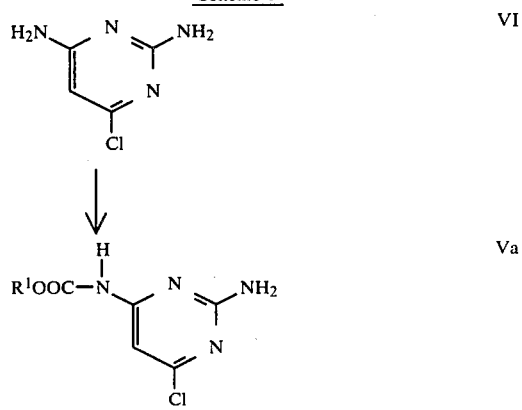

The known 2,4-diamino-6-chloropyrimidine of formula VI can be converted into a compound of formula Va by reaction with an azole derivative of the formula

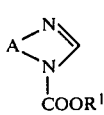

wherein $R^1$ is as previously described and A is a group of the formula

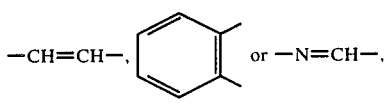

whereby the nitrogen atom in the latter case is situated in the 2-position.

The reaction of the compound of formula VI with an azole derivative of formula X is carried out according to known methods. Conveniently, the anion of the compound of formula VI is reacted with the azole derivative of formula X. The anion of the compound of formula VI is advantageously prepared in situ by reaction with a base. Bases such as alkali metal hydrides, for example, sodium hydride, alkali metal amides, for example, sodium amide or potassium amide, also lithium diisopropylamide, potassium tert.butylate and the like, are suitable for this purpose. The reaction is carried out in a solvent which is inert under the reaction conditions at a temperature in the range of from about −25° C. to about room temperature, preferably in the range of from about 0° to about 15° C. As solvents there come into consideration dimethylformamide, a saturated hydrocarbon, for example, hexane, an aromatic hydrocarbon, for example, benzene, toluene or xylene, an ether, for example, diethyl ether, dioxane or tetrahydrofuran, and the like.

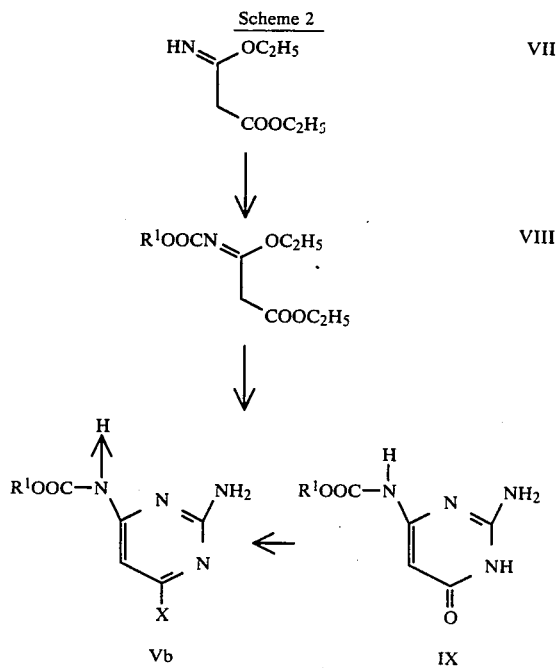

A compound of formula Vb can be prepared in three steps from the known ethyl β-amino-β-ethoxyacrylate of formula VII which, in turn, is readily accessible by the addition of ethanol to ethyl cyanoacetate.

In the first step, the ethyl β-amino-β-ethoxyacrylate of formula VII is reacted with a chloroformic acid ester of formula III hereinbefore. The reaction is carried out in an inert solvent or solvent mixture in the presence of an acid-binding agent. Chlorinated hydrocarbons, such as, methylene chloride or chlorform, aromatic hydrocarbons, such as, benzene or toluene, ethers, such as, tetrahydrofuran or dioxane, and the like or mixtures thereof are suitable solvents for the present purpose. As acid-binding agents there come into consideration bases such as triethylamine, ethyldiisopropylamine, N-methylmorpholine, N-ethylmorpholine, pyridine, picoline and the like. If the reaction is carried out in the presence of a liquid base, then this can also serve as the solvent. The reaction is conveniently carried out at a temperature in the range of from about −10° to about 50° C., preferably at about room temperature. In order to accelerate the reaction, it is conveniently carried out in the presence of 4-dimethylaminopyridine or 4-pyrrolidinopyridine as a catalyst.

In the second step, the compound of formula VIII obtained is condensed with guanidine hydrochloride under ring-closure in a solvent which is inert under the condensation conditions, preferably an alcohol, such as, methanol, ethanol, isopropanol and the like, at a temperature in the range of from about −10° to about 40° C., preferably at about room temperature, in the presence of a base such as an alkali metal alcoholate, for example, sodium methylate or sodium ethylate, an alkali metal hydroxide, for example, sodium hydroxide or potassium hydroxide, an alkaline earth metal hydroxide, for example, calcium hydroxide, and the like. The condensation is preferably carried out in the presence of an alkali metal alcoholate, and it will be appreciated that in this case the condensation is carried out in the alcohol which corresponds to the alcohol component of the alkali metal alcoholate. In order to avoid side-reactions, the condensation is carried out in the presence of an equimolar amount of base.

In the third step, a compound of formula IX is reacted with an arylsulfonic or alkylsulfonic acid halide or alkyl ester, preferably a chloride or methyl ester, in the presence of an excess of base. Organic bases, such as, ethyldiisopropylamine, triethylamine, N-methylmorpholine, N-ethylmorpholine, pyridine, picoline and the like or inorganic base, such as, alkali metal hydroxides and alkaline earth metal hydroxides, for example, sodium, potassium or calcium hydroxide, and the like are suitable bases for this purpose. The reaction is carried out at a temperature in the range of from about −10° to about 40° C., preferably about at room temperature, in an inert organic solvent such as a chlorinated hydrocarbon, for example, methylene chloride or chloroform, an ether, for example, tetrahydrofuran or dioxane, acetone and the like.

The Examples which follow further illustrate the invention. All temperatures are given in degrees Centigrade, unless otherwise stated.

EXAMPLE 1

Preparation of methyl 2-amino-6-[3,6-dihydro-1(2H)-pyridyl]-4-pyrimidinecarbamate-3-oxide Ethyl β-amino-β-ethoxyacrylate is obtained as a thick oil from 226 g of ethyl cyanoacetate and ethanol according to the procedure described by S. A. Glickmann and A. C. Cope, J. Am. Chem. Soc. 67, 1017 (1945).

79.5 g (0.5 mol) of ethyl β-amino-β-ethoxyacrylate are dissolved in 800 ml of absolute methylene chloride and the solution is treated with 2.0 g of 4-dimethylaminopyridine and 56.0 g of N-methylmorpholine. To the solution, cooled to −15°, is added dropwise a solution of 77 ml of methyl chloroformate in 500 ml of absolute methylene chloride. The mixture is stirred at room temperature overnight and thereafter evaporated under reduced pressure. The residue is dissolved in ether and the non-soluble crystalline salt is filtered off under suction. The ethereal solution is evaporated under reduced pressure. The residual methyl[1-ethoxy-2-ethoxycarbonyl)ethylidene]carbamate is sufficiently pure for use in the next step without purification.

250 ml of 2N methanolic sodium methylate solution are added dropwise to a solution of 48.0 g (0.5 mol) of guanidine hydrochloride in 700 ml of methanol. After filtering off the sodium chloride under suction, the clear solution obtained is added to a solution of 113.9 g of crude methyl[1-ethoxy-2-ethoxycarbonyl)ethylidene]-carbamate in 500 ml of methanol. Thereafter, a further 250 ml of 2N methanolic sodium methylate solution are added dropwise. The mixture is stirred at room temperature for 3 hours and thereafter evaporated under reduced pressure. The residue is dissolved in water and the solution is adjusted to pH 5 with glacial acetic acid, whereby there separates a thick precipitate which is carefully washed with water. There is obtained methyl 2-amino-1,6-dihydro-6-oxo-4-pyrimidinecarbamate of melting point >300°.

65 g (0.34 mol) of p-toluenesulfonyl chloride are added within 10 minutes to a suspension, cooled to 0°, of 55.2 g (0.3 mol) of methyl 2-amino-1,6-dihydro-6-oxo-4-pyrimidinecarbamate in 600 ml of pyridine. After a clear solution has resulted, it is left overnight in the refrigerator. Thereafter, the solvent is evaporated at 25° under reduced pressure. The residue is dissolved in methylene chloride and the organic solution is washed with 3N hydrochloric acid and then with water, dried over sodium sulfate and evaporated under reduced pressure. The residue obtained is recrystallized from methanol/methylene chloride. There is thus obtained methyl 2-amino-6-[(p-toluenesulfonyl)oxy]-4-pyrimidinecarbamate of melting point 186°–188°.

61.1 g (0.314 mol) of 88% m-chloroperbenzoic acid are added to a suspension of 50.7 g (0.15 mol) of methyl 2-amino-6-[(p-toluenesulfonyl)oxy]-4-pyrimidinecarbamate in 1800 ml of methylene chloride and 300 ml of methanol. The solution, which becomes clear after 2 hours, is stirred at room temperature overnight and thereafter warmed to 40° for 8 hours. 1800 ml of hexane are added to this solution and the mixture is cooled to 0° overnight, whereby there forms a crystalline precipitate which is filtered off under suction and dried. The mother liquor is concentrated to approximately 400 ml under reduced pressure, there being obtained a further crystalline precipitate of methyl 2-amino-6-[(p-toluenesulfonyl)oxy]-4-pyrimidinecarbamate-3-oxide of melting point 144°–145°.

24.8 g (70 mmol) of methyl 2-amino-6-[(p-toluenesulfonyl)oxy]-4-pyrimidinecarbamate-3-oxide and 14.5 g (175 mmol) of 1,2,5,6-tetrahydropyridine are boiled at reflux under argon in 400 ml of chloroform. After 90 minutes, the resulting precipitate is filtered off and the chloroform solution is washed with water. The organic phase is separated, dried over sodium sulfate and evaporated under reduced pressure, whereby there is obtained a crystalline solid. A sample of this material is recrystallized from methylene chloride/ether. The thus-obtained methyl 2-amino-6-[3,6-dihydro-1(2H)-pyridyl]-4-pyrimidinecarbamate-3-oxide melts at 221°–223° with decomposition.

EXAMPLE 2

Preparation of methyl
2-amino-6-[(3,6-dihydro-1(2H)-pyridyl]-4-pyrimidinecarbamate-3-oxide 2.0 g of ethyl β-amino-β-ethoxyacrylate are dissolved in 30 ml of absolute methylene chloride and treated at −10° with 5 ml of methyl chloroformate in 20 ml of absolute methylene chloride. The mixture is stored at 0° in a refrigerator. Thereafter, the solvent is evaporated under reduced pressure. The residue is taken up in ether. The precipitate is filtered off under suction and the solution is evaporated under reduced pressure. A sample of the pure oil obtained is left overnight in a high vacuum.

2.08 g (11 mmol) of p-toluenesulfonyl chloride in 20 ml of acetone are added dropwise to a solution of 1.47 g (8 mmol) of methyl 2-amino-1,6-dihydro-6-oxo-4-pyrimidinecarbamate, 12 ml of 1N sodium hydroxide, 5 ml of water and 50 ml of acetone. The mixture is stirred at room temperature for 18 hours. After filtration of the precipitate, the solvent is evaporated under reduced pressure. The residue is dissolved in a mixture of ethyl acetate and water, the organic phase is separated, dried and evaporated under reduced pressure. Crystallization from methylene chloride/methanol yields pure methyl 2-amino-6-[(p-toluenesulfonyl)oxy]-4-pyrimidinecarbamate of meltig point 188°–189°.

6.75 ml of 40% peracetic acid are added dropwise at 0° to a suspension of 3.4 g (10 mmol) of methyl 2-amino-6-([p-toluenesulfonyl)oxy]-4-pyrimidinecarbamate in 120 ml of absolute ethanol. The mixture is stirred at room temperature for 48 hours and thereafter poured into an aqueous solution of sodium sulfite. Ethyl acetate is added thereto, the organic phase is separated, dried over sodium sulphate and evaporated under reduced pressure. The residue is recrystallized from methylene chloride/methanol, there being obtained methyl 2-amino-6-[(p-toluenesulfonyl)oxy]-4-pyrimidinecarbamate-3-oxide of melting point 144°–145°.

1.05 g (0.0127 mol) of 1,2,5,6-tetrahydropyridine are added to a suspension of 1.77 g (0.005 mol) of methyl 2-amino-6-[(p-toluenesulfonyl)oxy]-4-pyrimidinecarbamate-3-oxide in 50 ml of chloroform. The mixture is boiled at reflux for 18 hours. Thereafter, a further 0.16 g (0.002 mol) of 1,2,5,6-tetrahydropyridine are added thereto and the mixture is boiled for a further 4 hours. The solvent is evaporated under reduced pressure and the residue is recrystallized from chloroform/ethyl acetate/ether, there being obtained methyl 2-amino-6-[(3,6-dihydro-1(2H)-pyridyl]-4-pyrimidinecarbamate-3-oxide of melting point 174°–175°.

EXAMPLE 3

Preparation of methyl
2-amino-6-chloro-4-pyrimidinecarbamate-3-oxide 46.3 g (0.32 mol) of 6-chloro-2,4-diamino-pyrimidine are dissolved in 1000 ml of tetrahydrofuran and treated with 57.9 g (0.517 mol) of potassium tert.butylate. The gel-like precipitate is stirred at room temperature for 1 hour. A solution of 60.5 g (0.48 mol) of 1-methoxycarbonylimidazole in 100 ml of ether is added thereto at a temperature of 10° within 90 minutes. The mixture is thereafter stirred at 25° for a further 2 hours, the solvent is then evaporated under reduced pressure and the residue is dissolved in ethyl acetate. The organic solution is washed with cold water and dried over sodium sulfate. After evaporation of the solvent under reduced pressure, the residue is crystallized from acetone/ether. After recrystallization from chloroform/methanol/hexane, there is obtained methyl 2-amino-6-chloro-4-pyrimidinecarbamate of melting point 225°–226°.

32 ml (0.20 mol) of 40% peracetic acid are added slowly to a solution of 20.2 g (0.10 mol) of methyl 2-amino-6-chloro-4-pyrimidinecarbamate in 500 ml of chloroform. The suspension obtained is warmed to 50° for 4 hours, whereby a clear solution gradually results. After cooling to room temperature, there is obtained by the slow addition of hexane a crystalline precipitate which is recrystallized from chloroform/methanol.

There is obtained methyl 2-amino-6-chloro-4-pyrimidinecarbamate-3-oxide of melting point 220°–221°.

EXAMPLE 4

Preparation of 2-isobutyl-4-methyl 6-[3,6-dihydro-1(2H)-pyridyl]-2,4-pyrimidinecarbamate-3-oxide (A) 7.95 g (30 mmol) of methyl 2-amino-6-[3,6-dihydro-1-(2H)-pyridyl]-4-pyrimidinecabamate-3-oxide are added to a solution of 300 ml of absolute methylene chloride, 100 ml of absolute tetrahydrofuran and 10 ml of ethyldiisopropylamine. The suspension obtained is cooled to 0° and treated dropwise with a solution of 4.4 g (30 mmol) of isobutyl chloroformate in 30 ml of absolute methylene chloride. After 1 hour, the organic solution is washed with water, dried over sodium sulphate and evaporated under reduced pressure. The residue is chromatographed on silica gel. Elution with a mixture of methylene chloride/acetonitrile (4:1) yields 2-isobutyl-4-methyl 6-[3,6-dihydro-1(2H)-pyridyl]-2,4-pyrimidinecarbamate-3-oxide of melting point 176°–177° (from methylene chloride/methanol/diethyl ether).

In an analogous manner there is obtained from methyl 2-amino-[3,6-dihydro-1(2H)-pyridyl]-4-pyrimidinecarbamate-3-oxide and ethyl chloroformate 2-ethyl-4-methyl 6-[3,6-dihydro-1(2H)-pyridyl]-2,4-pyrimidinedicarbamate-3-oxide of melting point 180°–181° (from methylene chloride/methanol);

and butyl chloroformate 2-butyl-4-methyl 6-[3,6-dihydro-1(2H)-pyridyl]-2,4-pyrimidinecarbamate-3-oxide of melting point 134°–135° (from methylene chloride/methanol).

(B) 19.9 g (75 mmol) of methyl 2-amino-6-[3,6-dihydro-1-(2H)-pyridyl]-4-pyrimidinecarbamate-3-oxide and 20 ml of methyl chloroformate are stirred very vigorously in a mixture of 1000 ml of methylene chloride and 1000 ml of water. At a temperature of 10° there is added dropwise a 28% sodium hydroxide solution so that the pH can be maintained at 7.5. After 2 hours, the two phases are separated, the aqueous phase is extracted with methylene chloride, the organic extracts are dried over sodium sulphate and filtered. The solution is treated with 20 ml of methanol, warmed to 60° overnight, evaporated to 100 ml and treated with ether. The precipitate formed is filtered off under suction and recrystallized from methylene chloride/ether. In this manner there is obtained dimethyl 6-[3,6-dihydro-1(2H)-pyridyl]-2,4-pyrimidinecarbamate-3-oxide which melts at 201°–202°.

(C) To a suspension of 1.0 g of 2-ethyl-4-methyl 6-[3,6-dihydro-1(2H)-pyridyl]-2,4-pyrimidinedicarbamate-3-oxide in 5 ml of methylene chloride and 50 ml of water is added dropwise 3N sodium hydroxide up to pH 12.8. After 1 hour, the aqueous solution is separated and acidified with 3N hydrochloric acid. The precipitate obtained is dissolved in ethyl acetate and chromatographed on silica gel. There is thus obtained methyl 5-[3,6-dihydro-1(2H)-pyridyl]-2-oxo-2H-[1,2,4]oxadiazolo[2,3-a]pyrimidine-7-carbamate of melting point 212° with decomposition (from methylene chloride/methanol).

This product can be obtained in an analogous manner from 2-isobutyl-4-methyl 6-[3,6-dihydro-1(2H)-pyridyl]-2,4-pyrimidinedicarbamate-3-oxide or from 2-butyl-4-methyl 6-[3,6-dihydro-1(2H)-pyridyl]-2,4-pyrimidinedicarbamate-3-oxide or from dimethyl 6-[3,6-dihydro-1(2H)-pyridyl]-2,4-pyrimidinedicarbamate-3-oxide.

EXAMPLE 5

Preparation of methyl 5-[3,6-dihydro-1(2H)-pyridyl]-2-oxo-2H-[1,2,4]oxadiazolo[2,3-a]pyrimidine-7-carbamate 35 ml of triethylamine are added to a suspension of 13.3 g (0.05 mol) of methyl 2-amino-6-[(3,6-dihydro-1(2H)-pyridyl)]-4-pyrimidinecarbamate-3-oxide in 600 ml of methylene chloride. After cooling to −20°, 32.5 ml (0.06 mol) of a 20% solution of phosgene in toluene are added dropwise within 2 minutes. After 10 minutes, the mixture is treated with 100 ml of 1N sodium hydroxide. The organic phase is separated and extracted with 1N sodium hydroxide. The aqueous extracts are acidified with 25% hydrochloric acid and the milky suspension is extracted with methylene chloride/methanol (95:5). The organic extracts are dried over sodium sulfate and evaporated under reduced pressure. 90 ml of acetonitrile are added to the residue. 5.6 g of dicyclohexylamine are added at 45° to the suspension obtained and the mixture is stirred at this temperature for a further 4 hours. The crystalline precipitate is filtered off under suction, washed with acetonitrile, carefully sucked dry and added to 180 ml of water. The suspension obtained is acidified to pH 3 with a solution of potassium bisulfate and stirred for a further 0.75 hour. After cooling to 0°, the precipitate is filtered off under suction, washed with water and dried at 60° under reduced pressure. After recrystallization from a mixture of methylene chloride/methanol/ether, there is obtained methyl 5-[3,6-dihydro-1(2H)-pyridyl]-2-oxo-2H-[1,2,4]oxadiazolo-[2,3-a]pyrimidine-7-carbamate of melting point 216°–218°.

EXAMPLE 6

Preparation of dimethyl 6-[3,6-dihydro-1(2H)-pyridyl]-2,4-pyrimidinedicarbamate-3-oxide 20.6 g of methyl 2-amino-6-[(p-tolylsulphonyl)oxy]-4-pyrimidinecarbamate are suspended in 120 ml of methanol and 720 ml of methylene chloride. While stirring there are added thereto at room temperature 20.5 g of m-chloroperbenzoic acid and after 6 hours a further 16.3 g of m-chloroperbenzoic acid. The mixture is stirred overnight and subsequently treated with 1.5 l of hexane, whereby a precipitate separates. The precipitate is filtered off under suction and dried, there being obtained crude methyl 2-amino-6-[(p-tolylsulfonyl)oxy]-4-pyrimidinecarbamate-3-oxide of melting point 139°–142°.

3.5 g of crude methyl 2-amino-6-[(p-tolylsulfonyl)oxy]-4-pyrimidinecarbamate-3-oxide are dissolved in 100 ml of methylene chloride and 50 ml of tetrahydrofuran. At 0° there are added thereto 2.2 g of N-methylmorpholine and subsequently 1.45 ml of methyl chloroformate in 20 ml of methylene chloride. The mixture is stirred at 0° for 1 hour and then at room temperature for 2 hours and thereupon treated with a small amount of methanol and water. The organic phase is separated, dried and evaporated. The residue is recrystallized from methylene chloride and ether, there being obtained pure dimethyl 6-[(p-tolylsulfonyl)oxy]-2,4-pyrimidinedicarbamate-3-oxide of melting point 178°–179°.

1.0 g of dimethyl 6-[(p-tolylsulfonyl)oxy]-2,4-pyrimidinedicarbamate-3-oxide is dissolved in 20 ml of chloroform and the solution is heated at reflux with 1 ml of 1,2,5,6-tetrahydropyridine. The cooled mixture is diluted with methylene chloride and washed with water. The organic phase is dried over sodium sulfate and concentrated. The residue is recrystallized from methylene chloride and methanol, there being obtained pure dimethyl 6-[3,6-dihydro-1(2H)-pyridyl]-2,4-pyrimidinedicarbamate-3-oxide of melting point 185°–187°.

EXAMPLE 7

Preparation of methyl 5-[3,6-dihydro-1(2H)-pyridyl]-2-oxo-2H-[1,2,4]oxadiazolo[2,3-a]pyrimidine-7-carbamate A solution of 226 g of ethyl cyanoacetate in 200 ml of absolute ethanol is saturated by introducing hydrochloric acid gas at 0°. The mixture is stirred at 0° overnight and then 1.5 l of tert.butyl methyl ether are added thereto. The ethyl β-amino-β-ethoxyacrylate hydrochloride which thereby precipitates is filtered off under suction, washed portionwise with 0.5 l of tert.butyl methyl ether and dried at 35° in vacuo. There is obtained ethyl β-amino-β-ethoxyacrylate hydrochloride, melting point 103°–104°.

A solution consisting of 96 g of ethyl β-amino-β-ethoxyacrylate hydrochloride, 800 ml of methylene chloride and 120 ml of N-methylmorpholine is warmed to 40°. While stirring there is added dropwise within 2 hours a solution of 65 ml of methyl chloroformate in 350 ml of methylene chloride. After completion of the addition, the mixture is stirred at 40° for a further 2 hours. Thereupon, the resulting salt is filtered off under suction and washed with about 50 ml of methylene chloride. The filtrate is evaporated at 40° in a water-jet vacuum. There is obtained crude methyl[(1-ethoxy-2-ethoxycarbonyl)-ethylidene]carbamate in the form of a pale yellow oil which is used immediately in the next step.

10 g of sodium are dissolved in 200 ml of absolute methanol, whereupon the solution is treated with 30 g of guanidine hydrochloride. While stirring there is added thereto a solution of 50 g of methyl[(1-ethoxy-2-ethoxycarbonyl)ethylidene]carbamate in 150 ml of absolute methanol. The resulting suspension is stirred overnight and thereafter concentrated at 40° in a water-jet vacuum. 600 ml of water are added to the residue and the resulting suspension is adjusted to pH 5 with glacial acetic acid while stirring. The resulting precipitate is filtered off under suction, washed with 250 ml of water and dried at 50° in vacuo. There is obtained methyl 2-amino-1,6-dihydro-6-oxo-4-pyrimidinecarbamate which is uniform according to thin-layer chromatography.

A stirred suspension of 500 g of methyl 2-amino-1,6-dihydro-6-oxo-4-pyrimidinecarbamate in 1.45 l of N-methylmorpholine and 9 l of methylene chloride is heated to reflux temperature. Subsequently, 815 g of toluene-4-sulfonyl chloride are added thereto and the mixture is stirred at reflux for 16 hours. The mixture is evaporated at 40° in a water-jet vacuum and the residue is treated with 9 l of water. The insoluble material is filtered off under suction and washed firstly with 5 l of water and thereafter with 5 l of ether. After drying at 40° in vacuo, there is obtained light brown methyl 2-amino-6-[(p-tolylsulfonyl)oxy]-4-pyrimidinecarbamate of melting point 188°–190°. A sample recrystallized from acetonitrile has a melting point of 190°–192°.

350 g of methyl 2-amino-6-[(p-tolylsulfonyl)oxy]-4-pyrimidinecarbamate are suspended in 6.3 l of methylene chloride and 1 l of methanol. At room temperature there are added thereto 370 g of m-chloroperbenzoic acid and the mixture is stirred for a further 16 hours. The yellowish solution is subsequently extracted with 3 l of 2N soda solution. The aqueous phase is extracted with 1 l of methylene chloride. The combined organic phases are washed with 2 l of water and evaporated in vacuo. The crystalline residue is suspended in 1.5 l of ether while stirring. The pale yellowish crystals are filtered off under suction and washed with 0.5 l of ether. After drying at 40° in vacuo, there is obtained methyl 2-amino-6-[(p-tolylsulfonyl)oxy]-4-pyrimidinecarbamate-3-oxide.

150 g of methyl 2-amino-6-[(p-tolylsulfonyl)oxy]-4-pyrimidinecarbamate-3-oxide are suspended in 2 l of methylene chloride and 2 l of water while stirring. After cooling to 0°–5°, 50 ml of methyl chloroformate are added thereto. After stirring vigorously for about 10 minutes, the mixture is adjusted to a pH of 7–7.5 with about 150 g of sodium bicarbonate. The mixture is subsequently stirred at 0°–5° for a further 3 hours. The organic phase is separated and the aqueous phase is extracted with 1 l of methylene chloride. The combined organic phases are washed twice with 1 l of water each time, dried over sodium sulphate and evaporated in vacuo. There is obtained crude dimethyl 6-[(p-tolylsulfonyl)oxy]-2,4-pyrimidinedicarbamate-3-oxide which is used in the next step (a pure product of melting point 178°–180° can be obtained by digestion with ethyl acetate).

300 g of 1,2,3,6-tetrahydropyridine hydrochloride are treated with 300 ml of 3N sodium hydroxide and the liberated base is extracted with three 750 ml portions of chloroform. The organic phase is dried over sodium sulphate and filtered. 180 g of crude dimethyl 6-[(p-tolylsulfonyl)oxy]-2,4-pyrimidinedicarbamate-3-oxide are added to the filtrate while stirring. The mixture is heated to reflux for 3 hours. After completion of the reaction, the mixture is extracted with 2 l of water, whereupon the organic phase is dried over sodium sulfate and concentrated in vacuo. The residue is suspended in 200 ml of ethyl acetate while stirring for 0.5 hour. The crystallizate is filtered off under suction, washed with 50 ml of ethyl acetate of −5° and dried at 30° in vacuo. There is obtained dimethyl 6-[3,6-dihydro-1(2H)-pyridyl]2,4-pyrimidinedicarbamate-3-oxide of melting point 178°–180°.

300 g of dimethyl 6-[3,6-dihydro-1(2H)-pyridyl]-2,4-pyrimidinedicarbamate-3-oxide are added to a solution of 180 g of sodium chloride in 3.3 l of water. To the suspension obtained are added dropwise about 130 ml of 28% sodium hydroxide until a pH of 12.8–13 has been attained. After stirring for 2 hours, the precipitate formed is filtered off under suction and dissolved in 5 l of water. Any undissolved solid is separated using a sintered glass suction filter and thereafter the filtrate is cooled to 5°. During about 4 hours at this temperature a moderate stream of carbonic acid is conducted through the filtrate, whereby methyl 5-[3,6-dihydro-1(2H)-pyridyl]-2-oxo-2H-[1,2,4]oxadiazolo[2,3a]pyrimidine-7-carbamate precipitates. After suction filtration, the product is washed with about 5 l of water until the wash-water is free from chlorine ions and then dried at 50° in vacuo. The pure product obtained melts at 203°–205°.

We claim:

1. A compound of the formula

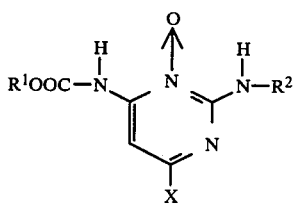

IV wherein X is p-toluenesulfonyloxy, benzenesulfonyloxy, p-bromobenzenesulfonyloxy or lower-alkylsulfonyloxy, $R^1$ is lower alkyl or lower alkoxy-lower alkyl, $R^2$ is hydrogen or —$COOR^3$ wherein $R^3$ is lower alkyl or lower alkoxy-lower alkyl, and $R^1$ and $R^3$ can be the same or different.

2. A compound in accordance with claim 1, wherein X is p-toluenesulfonyloxy or mesyloxy, $R^1$ is methyl and $R^2$ is hydrogen.

3. A compound in accordance with claim 2, methyl 2-amino-6-[(p-toluene-sulfonyl)oxy]-4-pyrimidinecarbamate-3-oxide.

4. A compound in accordance with claim 1, dimethyl 6-[(p-tolylsulfonyl)oxy]-2,4-pyrimidine-dicarbamate-3-oxide.

5. The compound, methyl 2-amino-6-[(p-toluenesulfonyl)oxy]-4-pyrimidinecarbamate.

* * * * *